(12) United States Patent
Gordon

(10) Patent No.: US 7,365,334 B1
(45) Date of Patent: Apr. 29, 2008

(54) AUTOMATED THREE DIMENSIONAL PATIENT TRACKING DURING MEDICAL IMAGING PROCEDURES

(75) Inventor: Jeff Gordon, San Diego, CA (US)

(73) Assignee: Digirad Corporation, Poway, CA (US)

( * ) Notice: Subject to any disclaimer, the term of this patent is extended or adjusted under 35 U.S.C. 154(b) by 85 days.

(21) Appl. No.: 11/239,635

(22) Filed: Sep. 28, 2005

Related U.S. Application Data

(60) Provisional application No. 60/614,121, filed on Sep. 28, 2004.

(51) Int. Cl.
*G01T 1/166* (2006.01)
(52) U.S. Cl. .................................... 250/363.04
(58) Field of Classification Search ............ 250/363.04
See application file for complete search history.

(56) References Cited

U.S. PATENT DOCUMENTS

| | | | | |
|---|---|---|---|---|
| 5,200,700 A | * | 4/1993 | Glover et al. ............... | 324/309 |
| 6,754,522 B2 | * | 6/2004 | Keren ......................... | 600/431 |
| 2003/0063292 A1 | * | 4/2003 | Mostafavi .................... | 356/614 |
| 2003/0184285 A1 | * | 10/2003 | Anderson et al. ......... | 324/207.17 |
| 2004/0171927 A1 | * | 9/2004 | Lowen et al. ............... | 600/410 |

* cited by examiner

*Primary Examiner*—David Porta
*Assistant Examiner*—Mark R Gaworecki
(74) *Attorney, Agent, or Firm*—Law Office of SC Harris

(57) ABSTRACT

A patient movement system is used to detect movement of the patient in multiple of different coordinates. The movement of the patient is obtained in real-time and correlated to times of medical images, and used to compensate those medical images for the actual patient movement. This can be used in place of post processing algorithms which do not have actual medical information.

18 Claims, 2 Drawing Sheets

AUTOMATED THREE DIMENSIONAL PATIENT TRACKING DURING MEDICAL IMAGING PROCEDURES

CROSS REFERENCE TO RELATED APPLICATIONS

The present application claims priority under 35 U.S.C. §119 to U.S. Provisional Application Ser. No. 60/614,121, filed Sep. 28, 2004, entitled AUTOMATED THREE DIMENSIONAL PATIENT TRACKING DURING MEDICAL IMAGING PROCEDURES, the disclosure of which is incorporated herein by reference.

BACKGROUND

Medical imaging systems may use nuclear materials, called radiopharmaceuticals, for the imaging. One such imaging system is single photon emission computed tomography, abbreviated as SPECT. Typical types of imaging may include single photon emission computed tomography or SPECT, Cardiac SPECT and Cardiac Gated SPECT, as well as others. Other techniques may include general nuclear medicine, which includes whole body and organ-specific planar imaging techniques, positron emission tomography ("PET") as well as magnetic resonance imaging.

Imaging systems of this type may be dependent on many variables. Patient motion during all types of Nuclear Medicine Imaging studies may cause misregistration of acquired projection data. The motion may result in the addition of artifacts to the reconstructed images.

For example, artifacts created by patient motion are a function of the time, degree, and type of motion as well as the number of camera detectors. These artifacts can cause misdiagnosis, due to the similarity of such defects to actual pathological conditions.

For example, patient motion induced-artifacts in 99mTc (metastable Technetium-99)-based myocardial perfusion SPECT images, may form a potential source of false-positive findings for coronary artery disease. However, analogous image distortion may occur in other medical imaging techniques, such as Positron Emission Tomography (PET), X-ray Computed Tomography (CT) and non-Cardiac Nuclear Medicine.

Post acquisition software motion correction has been used to attempt to correct images for patient motion. Cedars-Sinai MOCO is an existing package that decreases motion artifacts on SPECT imaging studies, such as myocardial perfusion SPECT images. MOCO uses a variety of post data acquisition algorithms to compensate the pre-reconstructed data sets for patient motion. MOCO attempts to mathematically shift the center of mass distribution of the post-acquired projections after each frame to compensate for patient motion distortion artifacts.

Software correction methods on two-dimensional projection data after image acquisition, however, have a limited ability to correct for certain kinds of movements: including patient twisting, organ rotation, and vertical slumping which is prevalent with upright patient seating orientation. Post acquisition software motion correction has other drawbacks and deficiencies that affect both diagnostic accuracy, technologist, and patient workflow. Some issues include:

a. The software operates on the motion-integrated data. The acquired projections effectively integrate patient motion for the entire frame scan. The software can only correct for the average position of the organ of interest during each frame. This may result in limited accuracy of the correction, as well as the inability to identify or discard large transient motions that may contaminate the data.

b. Mixed mode motion, such as patient twisting or organ rotation caused by patient respiration, may not be compensated correctly, because the software correction algorithms operate on the projection data as seen by the detectors, instead of the organ of interest directly. This limitation may result in either over- or under-correcting each orthogonal degree of motion in the study.

c. The inability of the software motion correction algorithms to account for, or notify the technologist of, uncorrectable motions during the study may even result in a need to rescan some patients. This in turn, may reduce the capacity of the imaging site to process patients.

d. Because of the inadequacies of present motion correction software, studies are frequently reconstructed both with and without motion correction software. The technologist must frequently analyze and prepare studies both with and without motion correction applied. This allows the physician to decide which method of reconstruction is most realistic and contains the fewest artifacts.

e. In exercise multigated blood-pool imaging, significant degradation of image quality occurs as a result of patient movement under the gamma camera. Motion correction devices using centroid tracking of x-y events emanating from the organ of interest cannot be applied to blood-pool studies, because cardiac contraction rotation masks the correctable patient motion component.

SUMMARY

The present application describes using a wireless three-dimensional tracker motion tracking device that produces streaming real time, three dimensional data that may include patient position and angular orientation information. The information is used to compensate study image data for the motion of the patient during an image acquisition and to compensate for that motion during the scan.

In an embodiment, the tracker can operate even when out of line of sight. An embodiment describes a magnetic device.

DETAILED DESCRIPTION

The general structure and techniques, and more specific embodiments which can be used to effect different ways of carrying out the more general goals are described herein.

The embodiment is described herein as being usable with cardiac SPECT type imaging. However, it should be understood that this the embodiment is usable used with any type of medical imaging that images parts or all of a patient, specifically nuclear medical imaging, and including specifically SPECT and/or PET. This technique may be used in other imaging modalities such as Positron Emission Tomography (PET), General Nuclear Medicine, including Planar, First pass, magnetic resonance imaging (MRI) and X-ray Computed Tomography (CT) where uncorrected patient motion may degrade the image. Each of these imaging techniques is generically referred to herein, as "medical imaging".

An automated Patient Motion Tracker to assess tracker accuracy, position and angular resolution with respect to the magnitude and direction of patient motion is disclosed. The tracker monitors the patient movement during imaging. In an embodiment, the tracker may monitor x, y and z movement, and also pitch, roll and yaw movement. The disclosed remote patient tracking device measures simultaneously updated position and orientation information in these 6 dimensions. The measurement may use Euler angles, for azimuth, elevation, or roll receiver orientation ($\alpha$, $\beta$, $\gamma$). This location description information may be updated to a computer data acquisition program in real time at an update rate. The update rate may be, for example, 60 updates/second. These six coordinates are sufficient to completely describe the object's position in space, and change in position from last update in space. The output position data are synchronized with the concurrent gamma ray image data in time. This can be used to manipulate and compensate the data spatially for the patient motion shift as seen at the detector head. The information from the tracker can be used as an automatic motion correction method that may be a substitute or an add-on to the post-processed motion correction software as presently used for medical imaging.

Figure 1:
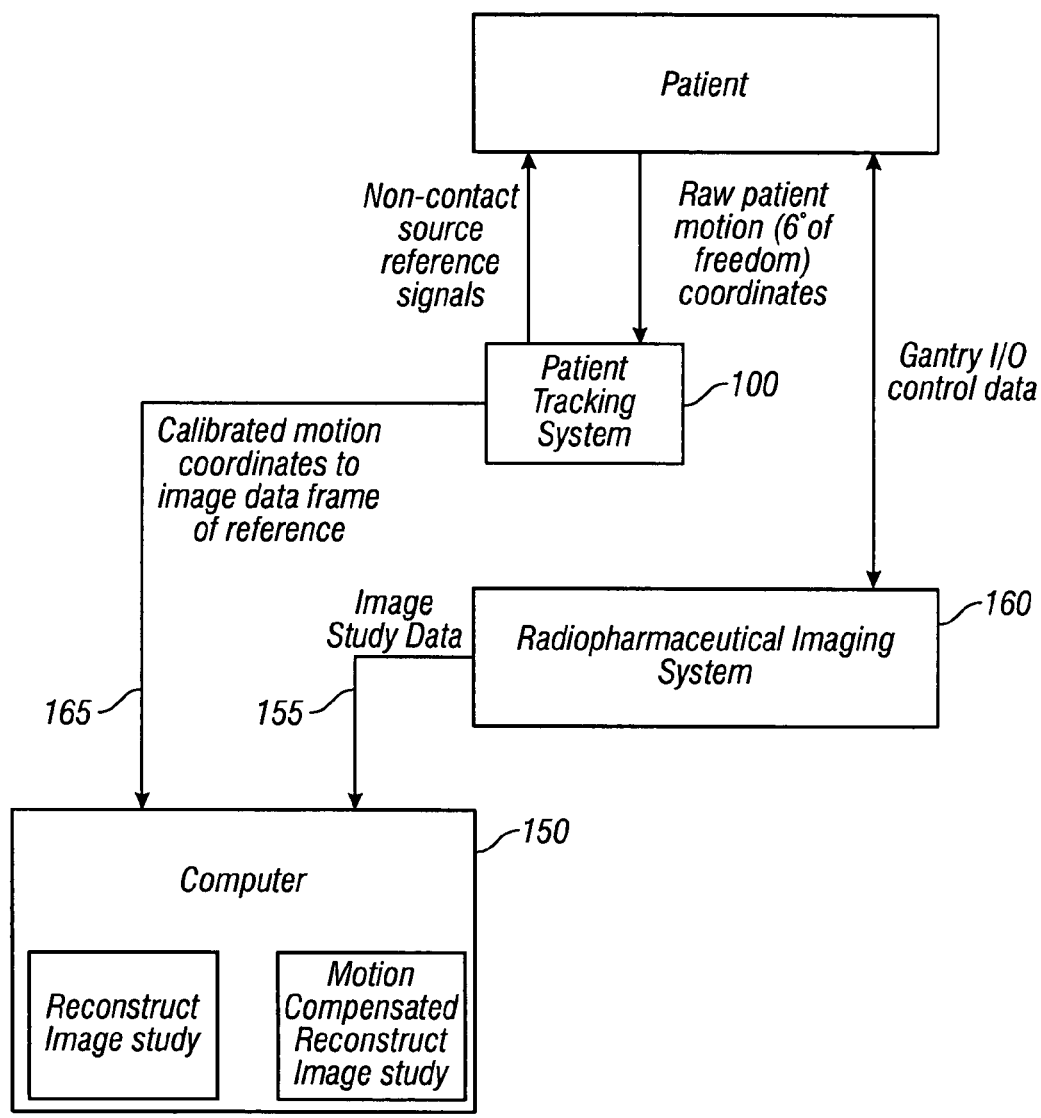
FIG. 1 illustrates the overall block diagram of the system.
Figure 2:
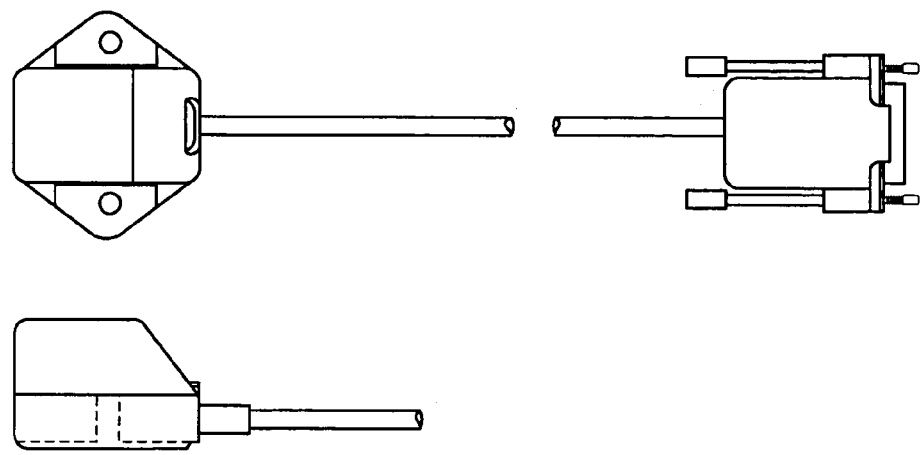
FIG. 2 illustrates a schematic image of a receiver that is affixed to the patient during the scan.

An embodiment is shown in FIG. 1. A tracking sensor 100 is attached to the patient being imaged. The attachment may use a tightly-fit binder to hold the sensor 100 to the patient. FIG. 2 shows an exemplary package that can be attached to the patient.

The sensor 100 is magnetically coupled to a field source 110. Movement of the sensor induces changes in the field source, which outputs are streamed in real-time to the computer 150. The computers described herein may be any kind of computer, either general purpose, or some specific purpose computer such as a workstation. The computer may be a Pentium class computer, running Windows XP or Linux, or may be a McIntosh computer. The programs may be written in C, or Java, or any other programming language. The programs may be resident on a storage medium, e.g., magnetic or optical, e.g. the computer hard drive, a removable disk or other removable medium. The programs may also be run over a network. The computer 150 also receives the medical image information 155 from the medical imaging system, e.g., imaging head 160. The computer 150 operates according to the flowchart of FIG. 4.

Figure 4:
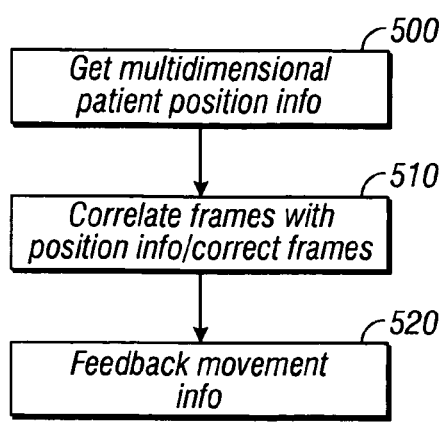
FIG. 4 shows a flowchart of operation carried out by the computer.

While FIG. 4 is shown as a flowchart being carried out on a computer, it should be understood that these techniques may be implemented in software, firmware or dedicated hardware.

The patient tracking system produces information 165 about the patient's position in 6 positional and rotational coordinates, forming 6 degrees of freedom. 500 illustrates the computer receiving multidimensional patient position information. The computer 150 uses this freedom information to correct raw patient image data 155 for patient motion before additional image processing occurs. At 510, the system correlates frames with the position information, and corrects the images at different times with the specific position of the patient at those different times.

Because correction of the position is carried out, the patient may not require binding restraints to suppress patient motion, or at least these bindings may be less intrusive, thereby improving patient comfort.

The data from the sensor may also be used to feed back information at 520. The information may be communicated to different people, e.g., to the technologist telling the technologist that they should intervene because there is too much patient motion. The information may alternatively be fed back to the patient itself to assist them in self compensating for their movement.

Tracker measurements provide a true position measurement of the organ of interest with respect to the body itself, including position changes resulting from twisting and organ rotation. Tracker measurements may permit a more accurate assessment of patient motion and produce a more accurate correction compared to the present state-of-the-art motion software correction used in Nuclear Medicine. Tracker measurements can produce real-time, updated streaming patient positioning information. These measurement are synchronized with each imaging data collection at any time by the acquisition module.

Therefore, for each discrete time period, an image is obtained, as well as a position of the body (in 6 directions) for that time period. The movement from any previous time period can be more exactly compensated. This therefore may enable many possibilities for dynamic image correction that may be post-processed motion correction algorithms.

The ability to obtain real-time data may open the door for new applications of medical imaging. One such application is respiratory gating, where the cardiac image data is corrected for artifacts resulting from breathing motion. Respiratory gating may also be used for real-time rejection of data resulting from excessive patient motion by detecting and generating respiratory gates to bin the data.

The first embodiment, described above, senses electromagnetic fields by magnetic induction to determine the position and orientation of the remote object. For brevity, the description below will employ the commonly used Cartesian (x, y, z) coordinate system. Orientation means direction in relationship to that position and may be fully described by three additional parameters or angles. For brevity, the description below will employ the commonly used Euler angle parameters alpha, beta, and gammarespectively known as azimuth (yaw), elevation (pitch), and roll.

Other embodiments may employ, singly or in any combination, magnetic linkage, stereoscopic optical imaging, inertial guidance tracking, sonar detection, magnetic induction tracking, infrared polarimetry or other techniques.

Another embodiment of a patient tracking system senses electro-magnetic fields by magnetic induction for the purposes of determining the position and orientation of a remote object for Automatic Image Frame Motion Correction. In this application, the tracker data are used to automatically correct patient data at the input acquisition data stream on a frame-by-frame basis. In this mode the tracking and correction process is essentially a substitute for the manual post-processing software correction. The Nuclear Medical Technician is not involved in correcting the motion of the patient.

A third embodiment employs the real-time patient motion correction data for respiratory motion correction. In this application, the motion tracker assesses intra-frame patient respiratory motion and provides a gating signal to the software. This gating signal is used by the image processing system to segregate and sum data based on their phase in the respiratory cycle. This capability enables the image processing system to motion-correct and generate reconstructed images taken at different phases in the breathing motion cycle, (i.e., the patient framed data may be sub-binned into time bins synchronized to the motion of the breathing cycle). This is directly analogous to presently used Cardiac Gated Studies, where the reconstructed cardiac 2D images are summed according to fixed phases in the cardiac R-R interval. Respiratory gating may remove cardiac artifacts that result from the patient's breathing motion and therefore improved diagnostic specificity and accuracy.

A fourth embodiment uses the real-time patient motion correction data for Extra-motion data rejection. Unlike post-processed software motion correction, real-time streaming motion correction may be used to reject short duration motions, such as coughing, spasm movements, and large voluntary patient displacements. The associated data may be removed in real-time from the acquisition stream and the scan may be lengthened to account for the removal of the high-motion corrupted data.

A fifth embodiment uses the real-time patient motion correction data for real-time motion-stabilized acquisition. The tracker data may be used to feed back information to the hardware gantry or display to enable stabilizing of images acquired during exercise, such as First Pass Stress Studies. In this case the patient could run on the treadmill while simultaneously being imaged using dynamic, short time frames that are corrected on the fly in the acquisition module, to generate planar images (i.e. blur corrected for patient motion).

A sixth embodiment employs the real-time patient motion correction data to provide real-time feedback to the technologist during a scan. The image correction and processing system may automatically alert the technologist that the scan should be aborted when the system detects that patient motion has exceeded pre-determined limits associated with excessive and uncorrectable motions. This has the benefit of allowing the patient to be rescanned quickly, thereby avoiding the risk associated with re-injecting the patient at a later time, which could arise if the study were found to be unusable after the fact.

A seventh embodiment employs the real-time patient motion data to correct Extra-cardiac nuclear imaging studies using a simultaneous combination of both respiratory gating and real-time motion suppression enabled by this device.

An eighth embodiment employs the real-time patient motion correction to provide patient feedback to help the patient stay still, as a method of biofeedback auto-correction. Motion-tracking information based on the degree and direction of patient motion can be displayed to the patient using a computer monitor or other appropriate output device during the scan. The patient may be alerted to correct or compensate for his or her motion in real time, thus obviating a need for motion correction after image acquisition. For instance, the patient may be alerted to sit straighter to counteract excessive slumping during the scan.

The magnetic induction linkage embodiment, is formed of a fixed magnetic-dipole transmitting device called a field source; a freely movable magnetic-dipole receiving device, which forms the receiver; and associated electronics as shown in FIG. 1. Both the transmitter and receiver antennas include three mutually-orthogonal and concentric coils of material. The loop diameters of the coils are kept very small compared to the distance separating the transmitter and receiver. Each loop to be regarded as a point or infinitesimal dipole. Exciting the loop antenna produces a field consisting of a far-field component and a near-field component, also referred to as an induction-field component. The far-field intensity is a function of both loop size and excitation frequency and decreases with the inverse of the distance ($1/r$) from the loop. The induction-field component intensity is not substantially frequency dependent, and decreases as the inverse cube of the distance ($1/r^3$). The quasi-static field is not detectable at long distances.

The transmitter is kept stationary and the sensed signals are input to a mathematical algorithm that computes the receiver's position and orientation relative to the transmitter.

In the system shown in FIG. 1, each loop of the transmitter antenna is in turn excited with a driving signal identical in frequency and phase. Each excitation produces a single axis transmitter dipole. The transmitter excitation is a pattern of three states. Exciting the transmitter thus results in an output a set of three linearly independent vectors. The three output (receiver) vectors contain sufficient information to determine the position and orientation of the receiver relative to the transmitter. Essentially, nine measurements are available to solve for the six unknowns—x, y, z for position and azimuth (yaw), elevation (pitch), and roll for orientation.

The Magnetic Linkage is the magnetic field or B field, is a vector quantity derived from the vector sum of the radial and tangential field components for a magnetic dipole. It contains both the magnetic moment vector m and the inverse cube of the range factors. There are three sensing coils and three magnetic moments with the resultant matrix, M, expressed by M=[m1.m2.m3]. Position and orientation are described by the voltages induced in the three receiver loops according to their sensitivity and orientation and given by the matrix quantity S=[s1.s2.s3]. Coupling between the Magnetic Linkage and Position and Orientation sensitivity produces nine voltages, giving rise to the input voltage matrix. These quantities are algebraically added to, or otherwise used to compensate, the voltage equation in the hardware, software, or firmware signal processing subsystem.

The position data are synchronized with the image data collected from the detectors in real time. The image data may then be position-adjusted in a plurality of ways such as on an event-by-event basis, between scan frames, or at any time interval desired for the application.

An embodiment of an automated tracker system based on magnetic linkage operates at a carrier frequency of 8.013 kHz. The tracker interfaces to the nuclear medical acquisition software host computer via RS-232 serial communication. A single receiver may be operated at the fastest available update rate (60 Hz) and must be synchronized with the computer input terminal via a settable baud rate. The information in this paragraph describes only one embodiment, and does not limit the hardware that can be used with other embodiments.

Transmitter/receiver cable connections and software configuration commands are issued to control the transmitter and data flow.

FIG. 2 is a drawing of one embodiment of a receiver, to be affixed to a patient, with dimensional information. The associated embodiment of a transmitter has a width of 2.15" (5.5 cm.), a length of 2.15" (5.5 cm.), a height of 2.3" (5.8 cm.), and a weight/mass of 0.6 lb (0.27 kg).

Figure 3:
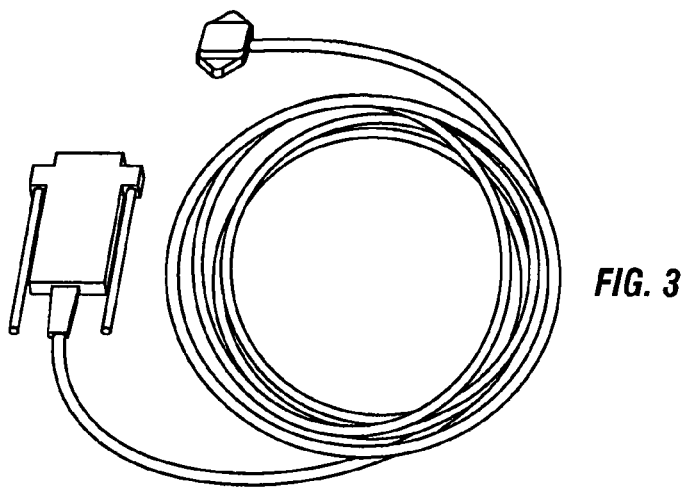
FIG. 3 shows an embodiment of a magnetic induction receiver and its cable.

FIG. 3 is a drawing of one embodiment of a receiver, to be mounted on a patient, with the cable attached to the receiver.

The embodiment described can provide an absolute static position accuracy of 0.24 cm RMS for the x, y, or z position of the receiver or receivers attached to the patient, and 0.75° RMS for azimuth, elevation, or roll receiver orientation. The system spatial and orientation resolution depends on the receiver-transmitter distance. In this embodiment, the resolution-to-distance coefficients are 0.038 mm spatial resolution per cm of separation at 30 cm separation, and 0.1° angular resolution per cm separation.

Although only a few embodiments have been disclosed in detail above, other embodiments are possible and the inventor (s) intend these to be encompassed within this specification. The specification describes specific examples to accomplish a more general goal that may be accomplished in other way. This disclosure is intended to be exemplary, and the claims are intended to cover any modification or alternative which might be predictable to a person having ordinary skill in the art. For example, other Also, the inventor(s) intend that only those claims which use the words "means for" are intended to be interpreted under 35 USC 112, sixth paragraph. Moreover, no limitations from the specification are intended to be read into any claims, unless those limitations are expressly included in the claims.

What is claimed is:

1. A method, comprising:
remotely detecting an absolute position and change in angular orientation of a patient during a time of medical imaging; and
correlating said position and orientation with the medical image detected during the time of the movement, to compensate the medical image for changes in the position, at a time that the medical image is obtained, wherein said remotely detecting comprises using a magnetic linkage type device which detects three orthogonal axes of motion, and wherein said remotely detecting operates outside a line of sight between said patient and a receiver.

2. A method as in claim 1, wherein said medical image is an image obtained from emissions from a single particle.

3. A method as in claim 1, further comprising attaching a magnetic linkage device to the patient using an attachment mechanism.

4. A method as in claim 1, further comprising using said information to compensate for respiratory movement within the patient.

5. A method as in claim 1, wherein said position and orientation are changed at each of a plurality of periodic intervals.

6. A method, comprising:
remotely detecting an absolute position and change in angular orientation of a patient during a time of medical imaging; and
correlating said position and orientation with the medical image detected during the time of the movement, to compensate the medical image for changes in the position, at a time that the medical image is obtained, wherein said medical imaging comprises an imaging of a patient based on an emission from a single photon source, and wherein said remotely detecting operates outside a line of sight between said patient and a receiver.

7. A method, comprising:
remotely detecting an absolute position and change in angular orientation of a patient during a time of medical imaging; and
correlating said position and orientation with the medical image detected during the time of the movement, to compensate the medical image for changes in the position, at a time that the medical image is obtained, wherein said absolute position includes six coordinates, including three orthogonal coordinates, and also including coordinates indicative of pitch, roll and yaw.

8. A method, comprising:
remotely, and from a position out of a line of sight, detecting an absolute position and change in angular orientation of a patient during a time of medical imaging; and
correlating said position and orientation with the medical image detected during the time of the movement, to compensate the medical image for changes in the position, at a time that the medical image is obtained, further comprising feeding back information indicative of patient movement.

9. A method as in claim 8, further comprising feeding back the information to the patient, to assist the patient in self compensating for patient motion.

10. A method, comprising:
remotely detecting an absolute position and change in angular orientation of a patient during a time of medical imaging; and
correlating said position and orientation with the medical image detected during the time of the movement, to compensate the medical image for changes in the position, at a time that the medical image is obtained, wherein said remotely detecting uses a magnetic linkage between two coils to detect six separate degrees of freedom of motions in the patient, where the first coil is attached to the patient, and the second coil is used to detect position of the first coil from a position outside a line of sight between said first coil and said second coil.

11. A medical imaging system, comprising:
a medical imaging receiver, which receives information indicative of a medical image of a patient;
a position receiver, which receives information indicative of a position and orientation of at least one area on the patient, at times correlated with times of receiving said medical image of the patient; and
an image compensating part, which compensates said medical image based on said position and orientation, wherein said position receiver is a magnetic linkage receiver, having a first part which receives information, and a second part, attached to the patient and outside of a line of sight from said first part, which produces information indicative of a position of the patient describing said movement according to 6 degrees of freedom including three orthogonal directions and three axial orientations.

12. A medical imaging system, comprising:
a medical imaging receiver, which receives information indicative of a medical image of a patient;
a position receiver, which receives information indicative of a position and orientation of at least one area on the patient, at times correlated with times of receiving said medical image of the patient; and
an image compensating part, which compensates said medical image based on said position and orientation, from an area outside of a line of sight, wherein said medical imaging receiver is a SPECT imaging head.

13. A medical imaging system, comprising:
a medical imaging receiver, which receives information indicative of a medical image of a patient;
a position receiver, which receives information indicative of a position and orientation of at least one area on the patient, at times correlated with times of receiving said medical image of the patient; and
an image compensating part, which compensates said medical image based on said position and orientation, wherein said image compensating part includes a computer that also feeds back information indicative of patient movement and produces a perceivable indicia that allows the patient to perceive an amount of their movement.

14. A medical imaging system, comprising:
a medical imaging receiver, which receives information indicative of a medical image of a patient;
a position receiver, which receives information indicative of a position and orientation of at least one area on the patient, at times correlated with times of receiving said medical image of the patient and storing said information along with information indicative of said times; and
an image compensating part, which compensates said medical image based on said position and orientation, by correlating frames with position information, and correcting the images at different times with the specific position of the patient at those different times, wherein said image compensating part compensates for respiratory movement.

15. A medical imaging system, comprising:
a medical imaging receiver, which receives information indicative of a medical image of a patient;
a position receiver, which receives information indicative of a position and orientation of at least one area on the patient, at times correlated with times of receiving said medical image of the patient and storing said information along with information indicative of said times; and
an image compensating part, which compensates said medical image based on said position and orientation, and correcting the images at different times with the specific position of the patient at those different times, wherein said first part is a magnetic coil, and said second part is a magnetic coil.

16. A medical imaging system, comprising:
a medical imaging receiver, which receives information indicative of a medical image of a patient;
a position receiver, which receives information indicative of a position and orientation of at least one area on the patient, at times correlated with times of receiving said medical image of the patient; and
an image compensating part, which compensates said medical image based on said position and orientation, wherein said position receiver produces 6 degrees of freedom of position and orientation information, including x, y and z movement, and also pitch, roll and yaw movement.

17. A method, comprising:
using a medical imaging part to obtain medical images of a patient produced by emissions from a nuclear material;
detecting movement of the patient from a position remote from the patient and producing an indicia indicative thereof;
correlating times of detecting said movement to times of obtaining said medical images; and
using said detecting movement to compensate the medical images that are obtained at a same time as a specific movement, to produce compensated medical imaging; and
using said compensated medical imaging to diagnose a medical condition in the patient, wherein said detecting movement comprises using a first magnetically linked part attached to the patient, using a second magnetically linked part distant from the patient to detect movement of the first magnetically linked part, and obtaining a multidimensional output from said second magnetically linked part indicative of multiple dimensions of said movement, including x, y and z movement, and also pitch, roll and yaw movement.

18. A method, comprising:
using a medical imaging part to obtain medical images of a patient produced by emissions from a nuclear material;
detecting movement of the patient from a position remote from the patient and producing an indicia indicative thereof;
correlating times of detecting said movement to times of obtaining said medical images; and
using said detecting movement to compensate the medical images that are obtained at a same time as a specific movement, to produce compensated medical imaging;
feeding back information indicative of movement to a patient to request said patient to reduce an amount of said movement; and
using said compensated medical imaging to diagnose a medical condition in the patient, wherein said movement comprises movement in three orthogonal directions, and orientation across 3 axes.

* * * * *